United States Patent [19]

Beeuwkes, III

[11] Patent Number: 4,872,449

[45] Date of Patent: Oct. 10, 1989

[54] QUICK-RELEASE DEVICE FOR JAW STABILIZATION

[75] Inventor: Reinier Beeuwkes, III, Ardmore, Pa.

[73] Assignee: Medical Products & Research, Houston, Tex.

[21] Appl. No.: 97,523

[22] Filed: Sep. 16, 1987

[51] Int. Cl.[4] .............................................. A61F 5/04
[52] U.S. Cl. .............................. 128/87 R; 128/89 A; 433/19
[58] Field of Search ................... 128/87 R, 89 A, 90, 128/91 R, 91 A; 433/19, 8

[56] References Cited

U.S. PATENT DOCUMENTS

| | | | |
|---|---|---|---|
| 817,946 | 4/1906 | Williams | 128/91 A |
| 1,797,481 | 3/1931 | Preston | 128/89 A |
| 2,103,942 | 12/1937 | Gillin | 128/91 R |
| 2,481,177 | 9/1949 | Tofflemire | 128/89 |
| 2,502,902 | 4/1950 | Tofflemire | 128/89 A |
| 3,654,702 | 4/1972 | Kelly, Jr. | 433/19 |
| 3,913,228 | 10/1975 | Wallshein | 32/14 A |
| 3,964,165 | 6/1976 | Stahl | 433/8 |
| 4,090,299 | 5/1978 | Williams | 32/14 A |
| 4,202,328 | 5/1980 | Sukkarie | 128/89 A |
| 4,230,104 | 10/1980 | Richter | 433/19 X |
| 4,364,380 | 12/1982 | Lewis | 128/89 A |

FOREIGN PATENT DOCUMENTS 601835 8/1934 Fed. Rep. of Germany.

Primary Examiner—Robert A. Hafer
Assistant Examiner—Kevin G. Rooney

[57] ABSTRACT

A quick-release maxillo-mandibular splint for patient jaw stabilization which includes a plurality of interfitting maxillary and mandibular connector plates which are adapted to be anchored in immovable relation with selected teeth of the patient. Each of the connector plates defines one or more connector elements which may be of tubular form and which are capable of being disposed in interengaging, aligned relation. A locking element such as a locking archwire is positioned with end portions thereof extending through the aligned tubular connector elements of the connector plates to thus retain the connector plates in immovable assembly to thus retain the jaw of the patient in properly occluded, immovable relation with the maxillary dental arch. In the event of an emergency requiring release of the maxillo-mandibular splint, the locking archwire is simply and efficiently forced from the tubular connector elements of the connector plates to thus permit movement of the patient's jaw.

9 Claims, 1 Drawing Sheet

QUICK-RELEASE DEVICE FOR JAW STABILIZATION

FIELD OF THE INVENTION

This invention relates to improvements in fracture and surgical appliances especially designed for the reduction and fixation of mandibular fractures. More specifically, the present invention is directed to a quick release maxillomandibular safety splint enabling efficient jaw stabilization and fixation following oral and maxillofacial surgery and yet providing for quick release of the splint as desired by the surgeon or for emergency conditions as desired by the surgeon or patient.

BACKGROUND OF THE INVENTION

In the event of mandibular fracture or in the event of oral and maxillofacial surgery, it is necessary to bring the teeth of the patient into proper occlusion and secure the jaw in stabilization to thereby secure the maxillary bond tissue in appropriate position for efficient healing. A number of developments have been conceived for stabilizing the upper and lower jaws of the patient following corrective surgery or bone positioning. One such development is exemplified by U.S. Pat. No. 2,481,17 of Tofflemire, which describes an intraoral fracture reduction appliance which stabilizes the mandibular arch relative to the maxillary arch and provides a structural bridge to secure the bones of the mandibular arch in proper assembly. The maxillary and mandibular sections of the apparatus are interconnected by elastic bands 32 that could be released to permit movement of the jaw. Under emergency conditions, however, it would be necessary to remove or cut eight elastic bands in order to permit movement of the jaw. Further, the surgeon or patient would need to have tools available to accomplish release of the appliance. In certain circumstances, such as when vomiting occurs, it is desirable to effect instant release of the splint in order that the needs of the patient may be attended to.

A conventional way of immobilizing either the maxillary or maxillofacial structures is to provide elongated bars such as arch bars, which are secured to the buccal and labial faces of certain ones of the teeth. The arch bars are then interconnected by fine twisted wire. The securing of arch bars with fine wires wrapped around certain ones of the teeth is particularly disadvantageous in that affixation of the wires takes considerable time to perform, during which the patient is often under a general anesthetic and is exposed to the hazards associated therewith. Moreover, the wires frequently break, are uncomfortable and are prone to trapping food particles. Other techniques include the provision of several small brackets which are secured to selected ones of the teeth and then interconnected by a complex set of archwires. In certain instances the archwires are strung between the upper and lower tooth sets to fix the jaw in a permanently closed condition until the corrective or healing process is sufficiently complete that the positions of the bones will be maintained without external support.

The procedure for attaching the aforementioned brackets, and stringing the archwires is complicated and often results in structural failure of the parts, thereby requiring second and third efforts to rebuild the structure before the corrective process is complete. Moreover, the complex structures associated with the prior art apparatus are often uncomfortable and irritating to the gingiva and other oral tissues and tend to trap food particles resulting in the adverse effects caused thereby. Pain and discomfort to the patient caused by present prior art devices are a major problem that needs to be overcome.

A more recent improvement entitled "Jaw Fixation Assembly" is the subject matter of U.S. patent application Ser. No. 864,006 filed by John B. Gatewood on May 16, 1986. In accordance with the teachings of Gatewood, U-shaped anchor members are positioned in anchoring relation with respective teeth of the maxillary and mandibular arches and receive retainer members which are in the form of grooved ball-like or button-like structures that are threaded onto the ends of the U-shaped members. Cross-wiring is then employed between the retainer members to provide a solid unmovable jaw fixation assembly. The jaw fixation assembly of Gatewood represents a substantial improvement over previous methods of jaw fixation, nevertheless it does not provide any means for quickly and efficiently effecting release of the upper and lower jaws such as in the case of emergency.

Accordingly, there has been a continuing need not only for appliances for improving and simplifying jaw fixation for efficient mobilization of the jaw structure but also for an appliance that may be effectively and quickly released to permit jaw movement such as during emergency conditions. The present invention provides these and other features.

SUMMARY OF THE INVENTION

It is a feature of the present invention to provide a novel quick-release maxillo-mandibular splint which may be simply and efficiently installed at the completion of oral and maxillofacial surgery for stabilizing the upper and lower jaws of the patient to permit efficient healing of the bone structure.

It is another feature of the present invention to provide a novel quick-release maxillo-mandibular splint that is capable of quick and efficient release by the surgeon or by the patient to thereby permit patient safety in the event emergency conditions should arise that requires movement of the jaw.

Briefly, the present invention provides a quick-release maxillo-mandibular splint appliance for jaw stabilization which incorporates a plurality of anchor devices that are intended to be secured in immovable relation with selected maxillary and mandibular teeth of the patient. Typically, upper and lower molars or bicuspids on respective sides of the fracture or surgery joint are selected as anchor teeth. Anchor devices are then secured to the anchor teeth in any suitable fashion. One suitable form of anchor device may conveniently take the form disclosed in the above mentioned U.S. Patent application Ser. No. 864,006. In such case, a U-shaped wire-like anchor member is provided having threaded straight leg portions joined by a U-shaped collar. Anchor members of this nature are placed about each selected tooth and retainer members in the form of polymer ball-like structures are threaded onto the respective threaded ends of each of the U-shaped member. The retainer members secure connector plates in immovable assembly with respective ones of the selected teeth. The connector plates are received by the straight leg portions of respective ones of the U-shaped anchor members. Each of the connector plates defines one or more connector elements that are adapted to be positioned in interengaging relation with the connector elements of opposed connector plates. In one form of the invention the connector elements may take the form of rolled tabs of the connector plate members which define lock passages. The connector elements of respective connector plates are positioned in assembly such that the lock passages are disposed in registry. A lock member is then positioned in locking engagement with the aligned and registered connector members or lock passages and functions to retain the respective connector plates in immovable assembly to thus fix the jaw in immovable relation with the maxillary arch. In one form of the invention the lock member may conveniently take the form of a connector archwire conforming to the shape of the alveolar arch of the patient. The locking archwire is positioned with its respective end portions inserted within the aligned lock passages of the connector elements. Should it become desirable to release the maxillo-mandibular safety splint, such can be accomplished quickly and efficiently simply by grasping the safety release archwire and exerting sufficient force to remove its end portions from the aligned passages of the connector elements. The safety splint can therefore be released for jaw movement within one or two seconds by the physician or by the patient to alleviate any emergency condition. Following the emergency, the maxillo-mandibular safety splint is then reinstalled simply by bringing the teeth of the patient into occlusion and positioning the connector elements of the connector plates in respective aligned registry. The safety release archwire is then reinserted into the aligned passages of the connector elements to restore the safety splint to its operative condition.

Although a particular maxillo-mandibular safety splint construction has been described and particular anchor members have also been described, such is not intended as limiting the spirit and scope of the present invention. Other types of anchor members may be attached to the selected teeth of the patient and other types of connector devices may be employed to firmly secure the connector plates in immovable assembly and to effect efficient release of the safety splint in the event movement of the jaw is necessitated such as by emergency conditions.

BRIEF DESCRIPTION OF THE DRAWINGS

So that the manner in which the above recited features, advantages and objects of this invention as well as others which will become apparent are attained and can be understood in detail, a more particular description of the invention, briefly summarized above, may be had by reference to the embodiments thereof that are illustrated in the appended drawings, which drawings form a part of this specification.

It is to be noted, however, that the appended drawings illustrate only typical embodiments of this invention and are therefore not to be considered limiting of its scope, for the invention may admit to other equally effective embodiments.

DETAILED DESCRIPTION OF PREFERRED EMBODIMENT

Figure 1:
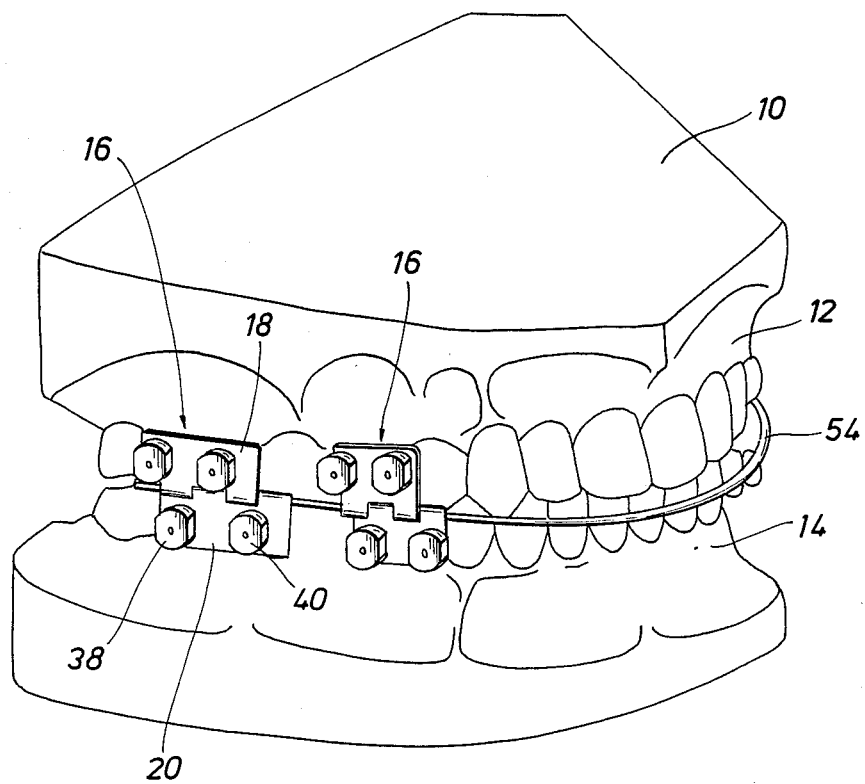
FIG. 1 is an isometric illustration of a maxillo-mandibular safety splint which is constructed in accordance with the present invention and shown in assembly with the maxillary and mandibular arches of the teeth of a dental model to thus fix the jaw in immovable assembly with the maxillary arch.
Figure 2:
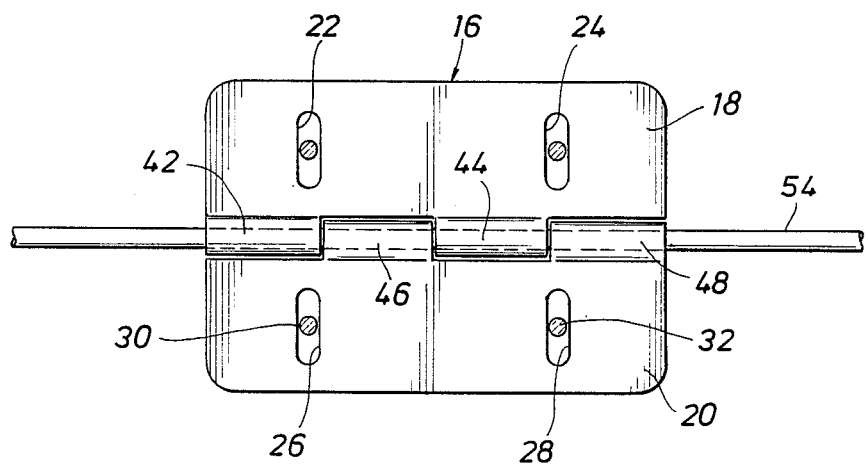
FIG. 2 is an elevational view of a pair of assembled connector plate elements being maintained in retained assembly by a safety release archwire.
Figure 3:
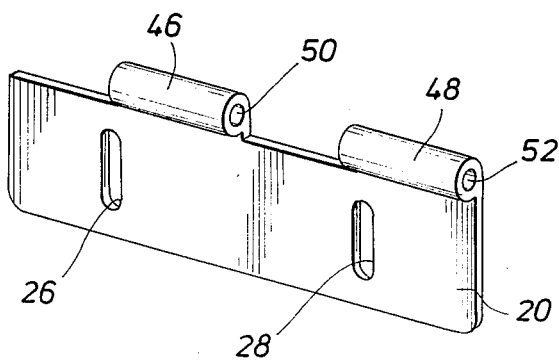
FIG. 3 is an isometric illustration of one of the retainer plates of FIG. 2 for illustration of the configuration of the tubular connector elements thereof.
Figure 4:
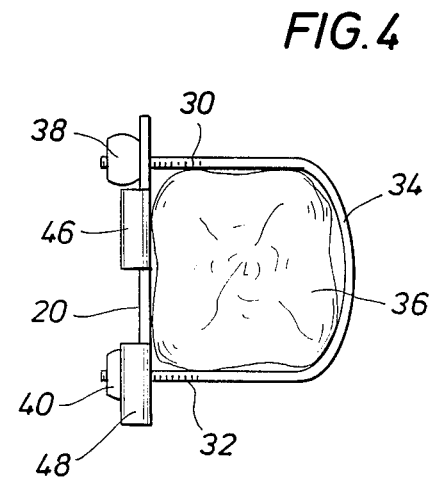
FIG. 4 is a plan view of a tooth of a patient illustrating assembly of anchor devices to the teeth to secure the connector plates in anchored assembly with the teeth.

Referring now to the drawings and first to FIG. 1, a model of a patient's teeth is shown at 10, which includes the maxillary aveolar arch 12 and a mandibular aveolar arch 14 with the respective teeth thereof. The maxillary and mandibular arches of the model 10 are shown to be retained in immovable assembly by a plurality of maxillo-mandibular safety splints, which are illustrated generally at 16. As is evident from FIG. 1 the safety splint 16 may be of any suitable mesial-distal length without departing from the spirit and scope of the present invention. A more detailed illustration of the maxillo-mandibular safety splint 16 is shown in FIG. 2 with the lower part of the splint being shown in the isometric illustration of FIG. 3. The splint 16 incorporates a pair of connector plates 18 and 20 which may be formed of a suitable polymer material or metal. The connector plates form anchor plates which are each adapted to be secured in immovable relation with respective anchor teeth as selected by the surgeon. Connector plate 18 is perforated to define a pair of spaced elongated slots 22 and 24 while the opposite connector plate 20 forms a pair of elongated slots 26 and 28. The slots 22–28 form adjustment slots to receive the respective straight threaded end portions 30 and 32 of a U-shaped anchor member 34 which is shown in FIG. 4 in assembly with a tooth 36. The threaded end portions 30 and 32 of the anchor member 34 may therefore be positioned in any suitable relation along the length of the respective elongated slots 26 and 28 as is evident from FIG. 2. Retainer elements 38 and 40 are threaded onto the respective threaded extremities 30 and 32 of the U-shaped anchor member 34 and thereby function to secure the respective connector plate in immovable assembly with the tooth to which the connector plate is anchored.

Each of the connector plates is provided with one or more connector elements such that respective connector plates 18 and 20 can be positioned in interfitting, aligned assembly for locking. According to one suitable form of the invention, as shown in the figures and in detail in FIG. 3, connector plate 18 is provided with a pair of spaced connector elements 42 and 44 while the opposed connector plate 20 is provided with a pair of spaced connector elements 46 and 48. As shown in FIG. 3, connector elements 46 and 48 are integral with the respective connector plate and are of generally tubular construction and define internal passages 50 and 52. The opposite connector elements 42 and 44 in such case are of like configuration and are capable of being assembled such that the respective internal passages thereof are disposed in interfitting, aligned registry. With the connector plates 18 and 20 positioned such that the connector elements thereof are in aligned registry, a safety release archwire 54 is positioned such that its respective ends extend through the registering passages of the connector elements and thus lock the connector elements in fixed assembly with one another as shown in FIGS. 1 and 2. The locking archwire may be composed of metal or non metal material suitable for intraoral application. As long as the retainer wire locking element remains in the position shown in FIGS. 1 and 2 the maxillo-mandibular safety splint will remain secured with the teeth firmly in occlusion and the jaw immobilized to thereby permit effective healing of the bone tissue. In the event an emergency condition arises requiring movement of the jaw or in the event the surgeon or another physician desires movement of the jaw, it is necessary to release the locking assembly of the splint. This is efficiently accomplished simply by applying force to the archwire locking device 54 to thus remove its respective extremities from the registering passages of the connector elements provided on the connector plates. Efficient release of the safety splint can therefore be accomplished within one or two seconds if need be, thus providing the patient with the capability of quickly and efficiently receiving appropriate medical care such as in the event of an emergency.

As mentioned above, during the splinting phase of maxillofacial surgery, the teeth of the patient are brought into occlusion and are then secured by appropriate splinting apparatus such that the jaw is positively immobilized during the healing process. When twisted wire or rubber band type splints are employed it is ordinarily extremely difficult for the surgeon to position the teeth of the patient in proper occlusion while at the same time causing the splinting apparatus to be affixed to the teeth or other structure to thus secure the jaw in properly occluded, immobilized relation with respect to the maxillary arch. The present invention effectively promotes simple and efficient installation of the maxillo-mandibular safety splint and permits efficient adjustment of the splint and jaw during installation. This is accomplished by placing the U-shaped anchor bands 34 in assembly with each of the selected teeth in the manner shown in FIG. 4. The respective connector plates 18 and 20 are then positioned with the respective threaded extremities 30 and 32 of the U-shaped anchor member being received by the elongated slots 26 and 28 of the respective connector plates. The retainer members 38 and 40 are then threaded onto the respective threaded ends of the U-shaped anchor members and are permitted to remain loosely in place. Thereafter, with all of the connector plates loosely assembled to the teeth the opposed connector plates are brought into aligned, registering relation in the manner shown in FIGS. 1 and 2 and the respective ends of the looking archwire 54 are inserted through the aligned passages of the connector plates. At this point the connector plates are locked to one another but are movable relative to the teeth by virtue of the elongated slots 26 and 28. After this has been accomplished, the jaw of the patient is moved relative to the maxillary arch such that the teeth are brought into proper occlusion and thus the jaw bones of the patient are positioned properly for efficient healing. After proper occlusion of the teeth and alignment of the jaw bones has been established the position of the U-shaped anchor member will have shifted or the connector plate will have shifted to establish a properly interfitting relation. The retainer elements 38 and 40 of the respective connector plates are then tightened to secure the connector plates in firmly fixed relation with the respective teeth. At this point the installation procedure is complete. Installation of the maxillo-mandibular safety splint can therefore be efficiently accomplished with minimal effort on the part of the surgeon. Further, in the event further adjustment of the patient's occlusion is desired, the retainer members can simply be loosened to thus loosen the safety splint relative to the teeth and, after appropriately positioning the teeth of the patient to establish proper occlusion, the retainer elements may be again tightened to firmly anchor the respective connector plates to the teeth.

As mentioned above, in the event it becomes desirable or necessary to unlock or release the maxillo-mandibular safety splint to thus permit movement of the jaw of the patient, such can be accomplished rapidly and efficiently simply by applying force to the safety release lock wire 54, thus extracting its ends from the aligned passages of the connector elements.

Although specific structures have been shown for formation of a novel maxillo-mandibular safety splint it is not intended that the present invention be limited to the specific structures that are shown and described. Any suitable anchor means may be employed to secure respective connector plates in immovable relation with the teeth of the patient. Further, the locking mechanism for securing the connector plates in immovable assembly and effecting efficient and quick release of the connector plates may take various other forms within the spirit and scope of the present invention.

It is therefore clearly evident that the present invention is one well adapted to attain all of the objects and advantages hereinabove set forth together with other objects and advantages that are inherent from a description of the apparatus itself.

It will be understood that certain combinations and subcombinations are of utility and may be employed without reference to other features and subcombinations. This is contemplated by and is within the scope of the present invention.

As many possible embodiments may be made of this invention without departing from the spirit and scope thereof, it is to be understood that all matters hereinabove set forth or shown in the accompanying drawings are to be interpreted as illustrative and not in any limiting sense.

What is claimed is:

1. A quick-release maxillo-mandibular splint appliance for jaw stabilization, comprising:
    (a) separate upper and lower means capable of being interconnected in immovable relation with selected upper and lower teeth of the patient; 344
    (b) tab means extending from said upper and lower means means to a permit registered and aligned assembly position to be formed between said upper and lower means to define a set of interleaved tab means along the jaw of the patient;
    (c) removable and releasable lock means for engaging said interleaved tab means to form an interlocked relation, between said separate upper and lower means, said lock means being easily removable to enable patient jaw movement;
    (d) wherein said separate upper and lower means each comprises:
        (1) an anchor member at least partially encircling a selected tooth of the patient,
        (2) a connector plate supported by said anchor member, and
        (3) retainer means received by said anchor member and securing said connector plate in immovable assembly with said selected tooth, and
        (4) wherein said connector plate defines an elongate planar member having a pair of spaced tab means formed into eyelets with aligned openings through said tab means;

(e) wherein said lock means comprises an elongate wire threadable through said eyelets;

(f) wherein said connector plate tab means comprise a pair of tabs spaced apart to enable interengaging relation with similar tabs on a mating connector plate; and (g) wherein said releasable lock means releasably engages said interengaged tabs to establish releasable interlocking relation between said interengaging opposed tabs.

2. A quick-release maxillo-mandibular splint appliance as recited in claim 1 wherein said tabs are equal in width and said connector plate supports at least two tabs spaced apart by a distance permitting insertion of a tab there between.

3. The quick-release maxillo-mandibular splint appliance as recited in claim 2 wherein said tabs have tubular eyelets and defined locking passage means, and locking passage means being disposed in aligned registry with locking passage means of an opposing connector plate to thus secure said opposed connector plates in releasable assembly.

4. A quick-release maxillo-mandibular splint appliance as recited in claim 3 wherein said releasable lock means is a safety release archwire having end portions that are receivable within aligned and registering passages means of said interengaged tab eyelets to thus secure said opposed connector plates in releasable assembly.

5. A quick-release maxillo-mandibular splint appliance as recited in claim 4 wherein said upper and lower means each includes a connector plate having two tabs therein and said tabs connect serially on said archwire.

6. A quick-release maxillo-mandibular splint appliance as recited in claim 1 wherein said connector plate has an elongate adjustment slot means permitting variable positioning of said anchor member relative to said connector plate and relative to a selected tooth.

7. A quick-release maxillo-mandibular splint appliance as recited in claim 6 wherein:

(a) said anchor member is a U-shaped member with extremities thereof extending through said elongate slot means of said connector plate; and (b) said retainer means is received by said extremities of said anchor member to secure said connector plate immovably relative to a selected tooth.

8. The quick-release maxillo mandibular splint appliance for jaw stabilization of claim 1 further wherein said separate upper and lower means include means for attachment in an immovable relation with selected upper and lower teeth selected to position said tab means from said separate upper and lower means in alignment in interleaved fashion of said tab means, and including similar sets of said separate upper and lower means for the left side and the right side of the patient's jaw.

9. The apparatus of claim 8 wherein said tab means is a protruding tab from a connector plate comprising said upper and lower means, and said protruding tab terminates in an edge located rolled eyelet defining an axial passage therethrough and said eyelet has a length coinciding with the width of said tab, and said upper and lower means are positioned on selected teeth to permit tabs to define a common axial passage in interlocking relationship.

* * * * *